(12) United States Patent
Lai

(10) Patent No.: US 6,179,422 B1
(45) Date of Patent: Jan. 30, 2001

(54) OPTICAL TRACKING DEVICE

(76) Inventor: Ming Lai, 1190 Encinitas Blvd., Encinitas, CA (US) 92024

( * ) Notice: Under 35 U.S.C. 154(b), the term of this patent shall be extended for 0 days.

(21) Appl. No.: 09/300,194

(22) Filed: Apr. 27, 1999

Related U.S. Application Data

(60) Provisional application No. 60/083,248, filed on Apr. 27, 1998.

(51) Int. Cl.7 ......................................................... A61B 3/14
(52) U.S. Cl. ............................................................... 351/210
(58) Field of Search ..................................... 351/206, 208, 351/209, 210, 221; 250/235; 356/445, 446, 447; 359/385

(56) References Cited

U.S. PATENT DOCUMENTS

| | | |
|---|---|---|
| 4,764,005 | 8/1988 | Webb et al. . |
| 4,856,891 | 8/1989 | Pflibsen et al. . |
| 5,028,802 * | 7/1991 | Webb et al. ........................ 250/235 |
| 5,098,426 | 3/1992 | Sklar et al. . |
| 5,345,281 | 9/1994 | Taboada et al. . |
| 5,360,424 | 11/1994 | Klopotek . |
| 5,410,376 | 4/1995 | Cornsweet et al. . |
| 5,430,505 | 7/1995 | Katz . |
| 5,620,436 | 4/1997 | Lang et al. . |
| 5,632,742 | 5/1997 | Frey et al. . |
| 5,645,550 | 7/1997 | Hohla . |
| 5,752,950 | 5/1998 | Frey et al. . |
| 5,782,822 | 7/1998 | Telfair et al. . |
| 5,923,399 * | 7/1999 | Van De Velde ..................... 351/221 |
| 5,966,197 * | 10/1999 | Yee ...................................... 351/210 |

* cited by examiner

Primary Examiner—George Manuel

(57) ABSTRACT

An optical tracking device and method are disclosed for tracking lateral movement of an object. A scanning probe beam and a time-resolved detection are implement in the disclosed technique. A particular application is for tracking the eye movement during a laser surgery.

20 Claims, 8 Drawing Sheets

OPTICAL TRACKING DEVICE

This application claims the benefit of US provisional application No. 60/083,248, filed on Apr. 27, 1998.

TECHNICAL FIELD

The present invention relates to tracking an object by optical means, and more specifically, to automatic monitoring and tracking a movable object such as an eye.

BACKGROUND

Monitoring and tracking a laterally movable object are important in many applications. In certain applications, it is desirable to have a tracking device not only to monitor the displacement of the object but also to follow the movement of the object without a significant delay. Tracking and following the eye movement during a laser eye surgery is an example of such applications.

Many eye-tracking devices have been developed for eye surgery with lasers, in particular, for photo-refractive surgery. A typical photo-refractive surgery scans an UV laser beam on the cornea to sculpture the profile of the corneal outer surface, one layer at a time. This procedure can correct various refractive disorders of the eye, including nearsightedness, farsightedness, and astigmatism.

Any eye movement during the surgery may adversely affect the outcome of refractive correction. Immobilizing the eye movement during a surgery has been proven difficult in practice. A device automatically tracking and compensating the eye movement is an attractive approach. For the nature of photo-refractive surgery, the tracking device needs to be fast, accurate, and reliable.

U.S. Pat. No. 5,620,436 discloses use of a video camera to monitor the eye's movement and to determine the position of an aiming beam on the eye. U.S. Pat. No. 5,632,742 teaches projecting four laser spots on the eye and using a set of peak-and-hold circuits to determine the position of the eye. In these designs, a ring shape reference is used for determining the eye position, and spatial stationary infrared beams are applied to illuminate the reference. Sophisticated imaging system and electronics, such as a CCD camera or four peak-and-hold circuits are implemented to determine the position of the reference. The ring shape references are practically either the limbus or the iris of the eye and the whole ring is needed as the reference for determining the eye position.

SUMMARY

Generally, any optically identifiable reference mark or indicator affix to an object can be used to indicate the position and movement of the object. The devices and methods disclosed herein apply an optical probe beam scanning repeatedly and rapidly over such a reference mark. A change in the position of the reference mark can then be determined by measuring the change in the delay between a predetermined reference time and the detected time at which the optical probe beam intercepts the reference mark. The reference mark can be artificially formed on the object, or alternatively, can be an inherent mark on the object.

For the application of eye tracking, a reference mark may be the limbus of the eye, which is the natural boundary between the transparent cornea and the white sclera. Optical scattering changes from one side of the limbus to the other significantly. Therefore the position of the limbus can be detected by measuring the timing of the change in the scattered light of the probe beam as the probe beam scans across the limbus. The devices and methods of the present disclosure will be described by examples of eye tracking using a section of the limbus as the reference mark.

In one embodiment, a section of the limbus is used as the reference mark and the x-y positions of the limbus are determined by two sets of linear positioning devices. The two linear positioning devices are set for measurement along two mutually orthogonal axes.

Each linear positioning device consists of a scanning beam generator, a detection assembly, and a processing electronics. The scanning-beam generator projects an infrared probe beam onto the eye and scans the probe beam across a section of the limbus repetitively. The detection assembly detects the infrared light scattered from the eye. The detected scattered-light signal is a time-resolved signal and has a sequence of sharp steps corresponding to the probe beam repeatedly across the limbus. The timing of each sharp step depends on the limbus position at the corresponding scan. The processing electronics converts the timing of the sharp steps into the positioning signal indicating the position of the eye.

With the positioning signal, a system computer can then generate a control signal to steer the surgical laser beam to follow the movement of the eye. Hence, accurate laser surgery can be achieved even though the eye may move during the surgery.

In this embodiment, about a quart of the limbus is used to determine the x and y positions of the eye. This is particularly important for a new type of refractive surgery so called LASIK, in which part of the limbus is obstructed during the surgery. This embodiment can use the limbus section that is not blocked and thus it can use the limbus as a reliable reference mark for LASIK.

DETAILED DESCRIPTION

Figures 1, 1A:
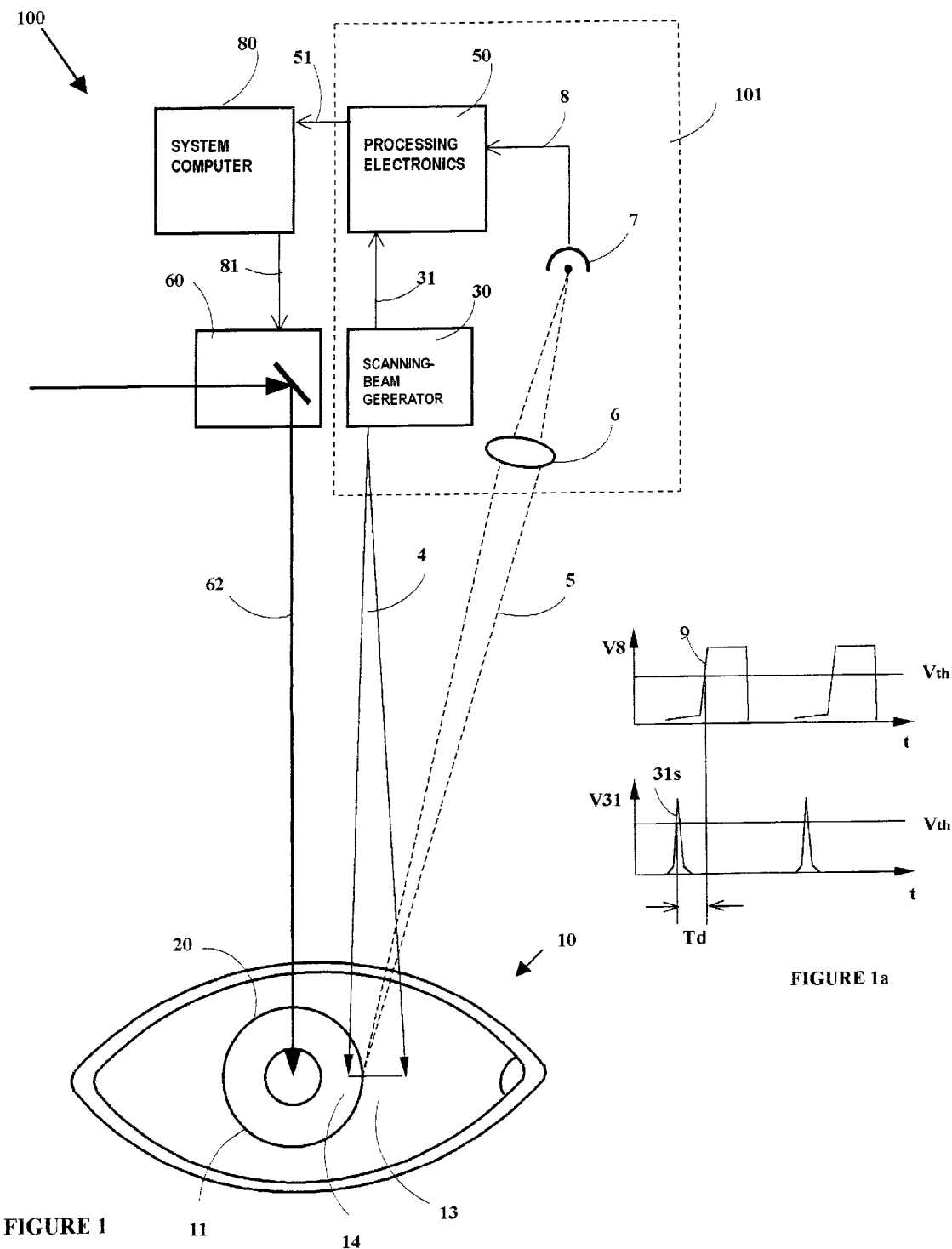
FIG. 1 is a schematic diagram showing one embodiment of an open-loop optical monitoring and tracking system.
FIG. 1a shows timing diagrams of the scattered-light signal from the eye and the reference signal generated by a scanning beam generator.

FIG. 1 shows a schematic diagram of one embodiment of an optical monitoring and tracking system 100 for an eye 10. The system 100 implements an open loop configuration that includes a position sensing module 101, a system computer 80, and a beam steering module 60 (e.g., a x-y scanner). The position-sensing module 101 projects a scanning probe beam 4 and monitors the position of the eye 10. The system computer 80 controls the beam steering module 60 to guide a surgical laser beam 62 to a desired position on the eye 10. As an open loop configuration, the scanning probe beam 4 dose not follow the movement of the eye 10 and only one beam steering module 60 is required.

For illustration purpose, the position-sensing module 101 shown in FIG. 1 is only a linear positioning device and is for monitoring one-dimensional eye movement only (e.g., along x-direction). To determine the eye's movement in two dimensions, a second set of linear positioning device is needed to monitor the movement of the eye 10 along a second different direction, e.g., the y-direction orthogonal to the x-direction.

The position-sensing module 101 comprises a scanning beam generator 30, a collection lens 6, a photo-detector 7, and a processing electronics 50. The limbus 11 of the eye 10 is used as a reference mark 20. The scanning-beam generator 30 projects a scanning probe beam 4 across the reference mark 20. The scanning probe beam 4 may repeatedly start from a fixed point and is scanned at a constant speed over a predetermined tracking range. The scanning-beam generator 30 also produces a reference signal 31 to indicate a reference point of the scanning.

The lens 6 is disposed at a proper position relative to the eye 10 to collect the scattered light 5. The photo-detector 7 receives and converts the scattered light 5 into an electrical signal, i.e., the scattered-light signal 8. The scattering from the sclera side 13 of the eye 10 is approximately 20 times stronger than that from the transparent cornea side 14. Hence, the intensity of the scattered light 5 exhibits a significant change when the probe beam 4 scans across the limbus 11. This intensity change of the scattered light 5, in turn, generates a sharp step in the scattered-light signal 8. The timing of this sharp step depends on the position of the eye 10.

In one implementation, an infrared laser beam (at 830 nm) of about 100 $\mu$W is used as the scanning probe beam 4 and the collection lens 6 having an aperture of about 18 mm is located about 30 cm away from the eye 10. Detector 7 receives a scattered-light power of about 20 nW when the probe beam 4 is on the sclera side.

FIG. 1a shows timing diagrams of the scattered-light signal 8 and the reference signal 31. The scattered-light signal 8 has a sequence of sharp steps and each sharp step 9 corresponds to a scan of the probe beam 4 across the limbus 11. The sharp step 9 has a time delay Td with respect to the reference point 31s of the scanning. This time delay Td depends on the position of the limbus 11 and varies as the eye 10 moves. The processing electronics 50, which may include a microprocessor, processes the reference signal 31 and the scattered-light signal 8 to determine this time delay Td for each scan. This time delay Td is then used to determine the position of the limbus 11. The lines Vth represent the threshold voltage for triggering.

To operate the tracking device 100, an initial time delay $Td_0$ or eye position is first registered and stored in the system computer 80. The time delay Td of subsequent scans is then compared with the initial time delay $Td_0$ to calculate a displacement of the eye 10. With this calculated displacement, the system computer 80 can generate a control signal 81 to drive the beam steering module 60 to steer the surgical laser beam 62 to follow the movement of the eye 10.

As an open loop device, the scanning probe beam 4 does not move with the eye 10. The beam steering module 60 can be used simultaneously to compensate the eye movement and to scan the surgical laser beam 62 on the eye 10. In this case, the control signal 81 may consist of a scanning signal and an offset signal. The scanning signal scans the surgical laser beam 62 in a predetermined pattern while the offset signal offsets the scanning to compensate for the eye movement. This open-loop device is relatively simple and is good for tracking small movement of the eye 10.

Figure 2:
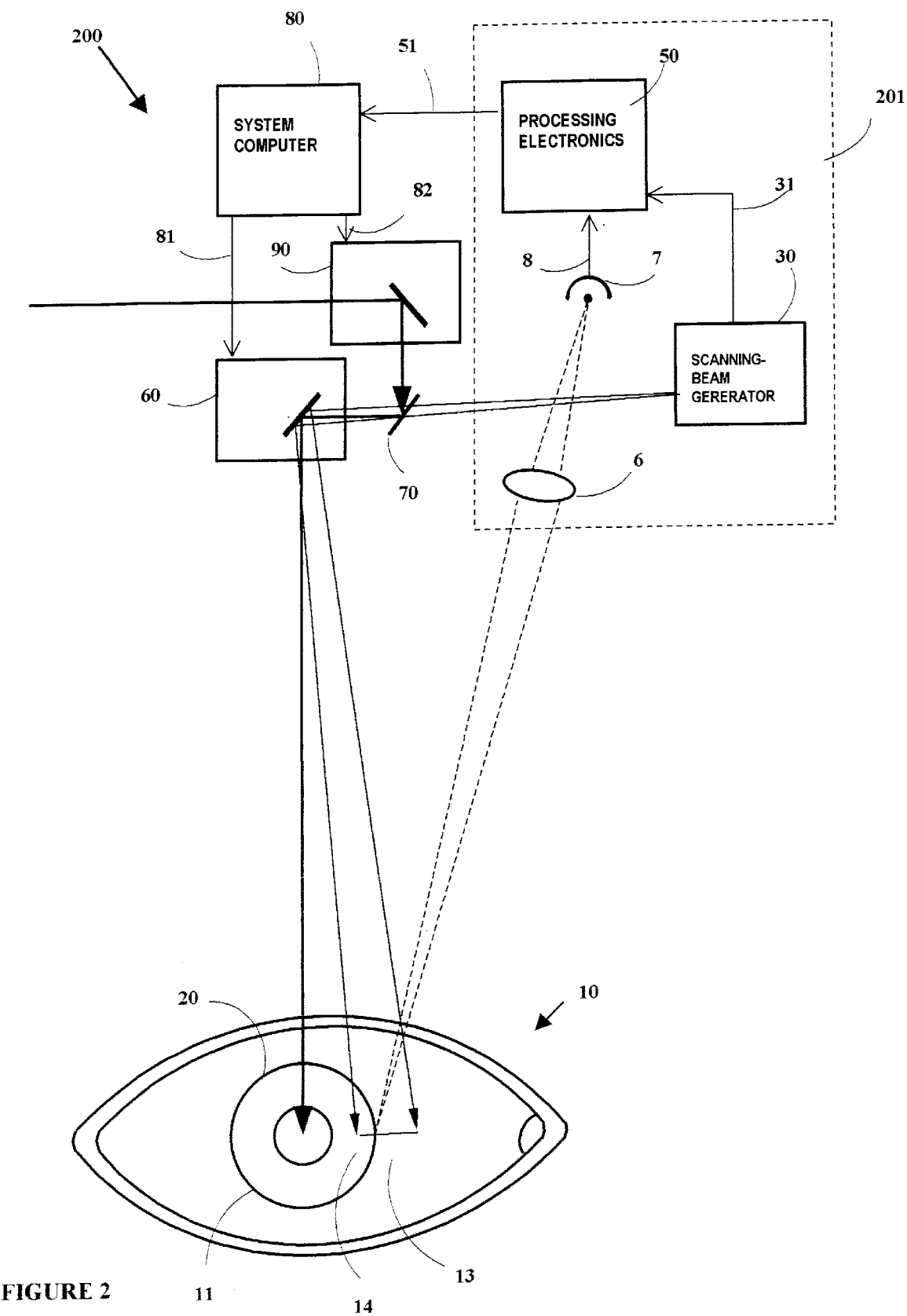
FIG. 2 is a schematic diagram showing an embodiment of a close-oop optical monitoring and tracking system.

FIG. 2 shows a schematic diagram of a close-loop tracking device 200. In the close-loop configuration, both the scanning beam 4 and the surgical beam 62 are steered to the eye 10 by a common steering module 60. Consequently, both the scanning probe beam 4 and the surgical laser beam 62 follow the movement of the eye 10.

In implementation, the scanning probe beam 4 is directed into the beam steering module 60 and reflected onto the reference mark 20 (i.e. the limbus 11). A dichromatic mirror 70 is placed in the path of the scanning probe beam 4 to couple the surgical laser beam 62 into the beam steering module 60. The dichromatic mirror 70 reflects light at the wavelength of the surgical laser beam 62 but transmits light at the wavelength of the scanning probe beam 4. The surgical laser beam 62 is reflected from the beam steering module 60 and projected onto the eye 10.

Again, the scattered light 5 from the reference mark 20 is collected by a lens 6 and detected by a photo-detector 7, which produces an output of scattered-light signal 8. Similar to the open loop device 100, the scatted-light signal 8 has a sharp step 9 corresponding to each scan of the probe beam 4 across the boundary of the reference mark 20. The sharp step 9 has a time delay Td with respect to the reference point 31s of corresponding scan. A processing electronics 50 determines this time delay Td for each scan.

To operate the tracking device 200, an initial time delay $Td_0$ or eye position is first registered and stored by the system computer 80. The time delay Td of later scans is then compared with the initial time delay $Td_0$. Any deviation of Td from $Td_0$ is used as an error signal to drive the beam steering module 60 such that to bring the error signal toward zero. Through this process, the beam steering module 60 deflects the scanning probe beam 4 to follow the movement of the eye 10. Seeing the same deflection as the scanning probe beam 4, the surgical laser beam 62 can thus impinge on any predetermined position of the eye 10 as if the eye remains stationary.

As a close loop device, the relative position between the trace of the scanning probe beam 4 and the reference mark 20 is kept constant during the operation. The beam steering module 60 is thus used solely for compensating the eye movement. A second beam steering module 90 is required to scan the surgical laser beam 62 on the eye 10 for surgery purpose. In this case, the control signal 81 to beam steering module 60 is simply the driving signal to compensate the eye movement. The control signal 82 to beam steering module 90 is simply the programmable signal to scan the surgical laser beam 62. The close loop device 200 is relatively more complicate but it can track a relative large displacement of the eye 10.

Figure 3A:
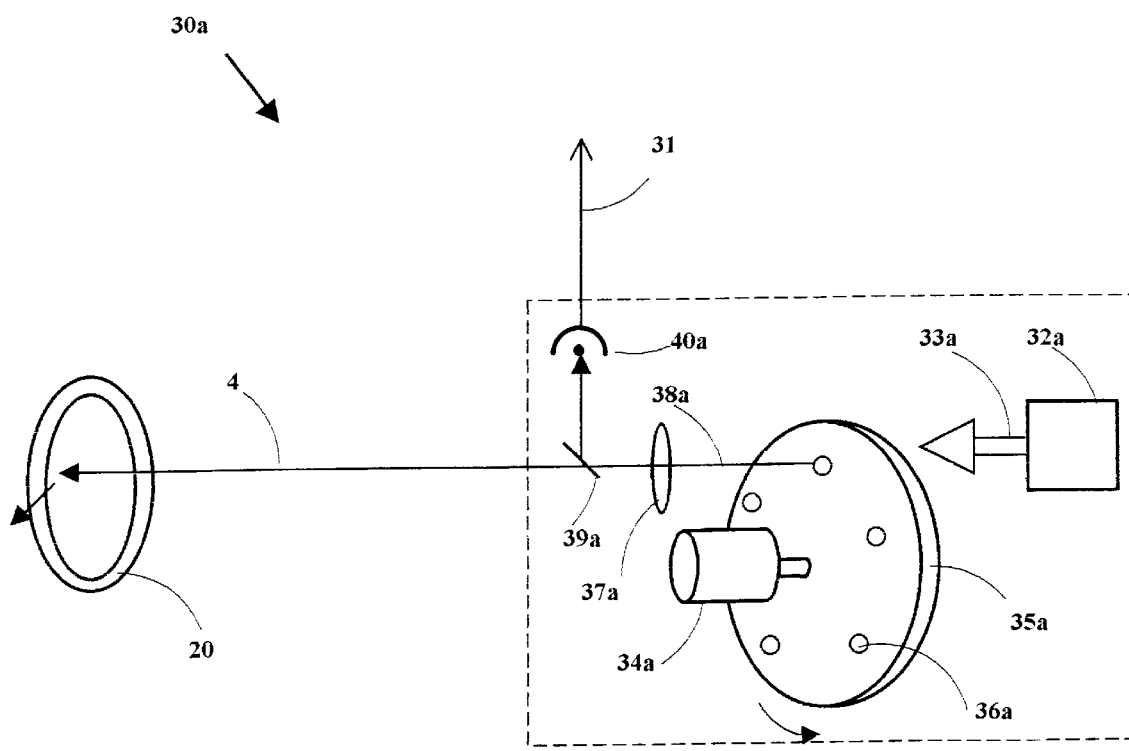
FIG. 3a is a schematic diagram showing one embodiment of a scanning-beam generator.

FIG. 3a shows one embodiment of a scanning-beam generator 30a that produces a scanning probe beam 4a. The generator 30a includes an infrared-light source 32a, which produces an infrared-light beam 33a projected onto a rotating blade 35a. The blade 35a has a set of pinholes 36a evenly distributed on a circle. A motor 34a drives the blade 35a at a constant rotation speed. The pinholes 36a are thus scanned across the infrared-light beam 33a at a constant speed.

A lens 37a focuses onto a reference ring 20 (i.e. the reference mark) the infrared-light beam 38a that is transmitted through the pinhole 36a. As the pinhole 36a is scanned across the infrared beam 33a, the image of the pinhole 36a is scanned across the reference ring 20. Thus, the transmitted infrared beam 38a may serve as the scanning probe beam 4 of FIG. 1.

A beam splitter 39a directs a small portion of the beam 38a onto a reference photo-detector 40a. This reference photo-detector 40a has a tiny light-sensitive area and the detected signal is thus a sequence of spikes as the split beam scans across the reference detector repetitively. The output signal from the photo-detector 40a defines a reference point of the scanning and serves as the reference signal 31 of FIG. 1.

In this embodiment, the infrared-light source 32a can be simply a light emitted diode. The repetition rate of the scanning probe beam 4 can be up to the kilohertz range. For example, the motor 34a may run at 100 rotation per second and the blade 35a may have 10 pinholes 36a on it.

Figure 3B:
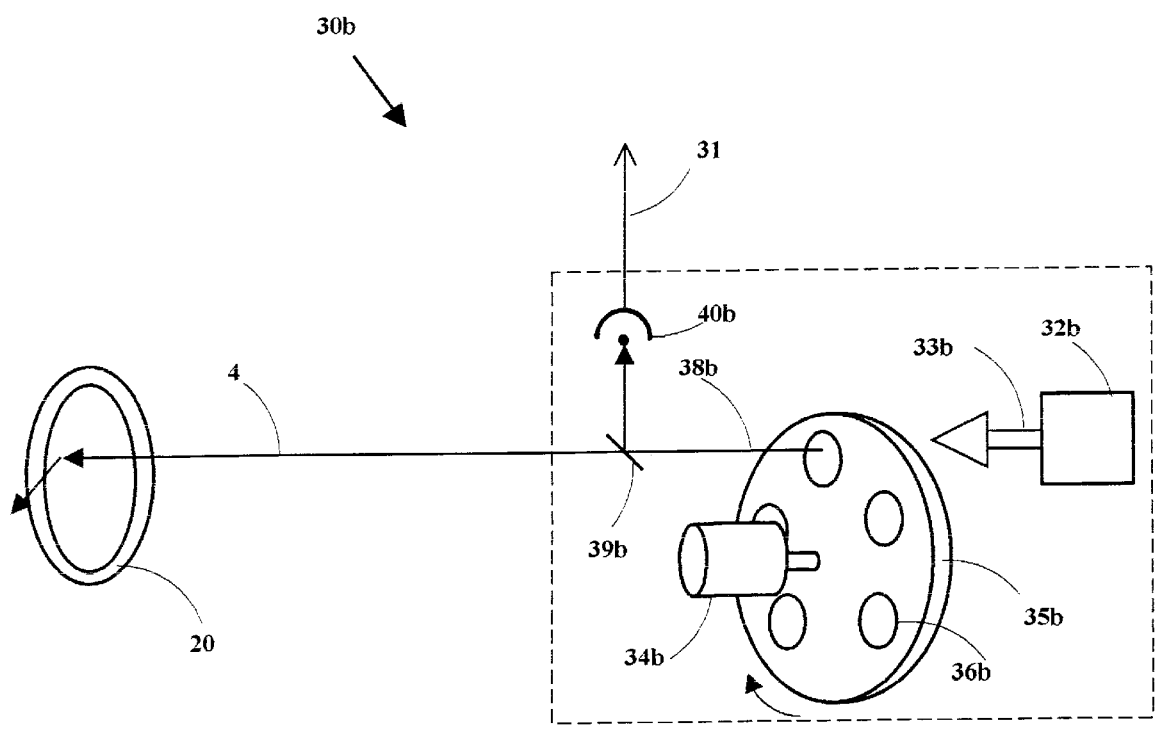
FIG. 3b is a schematic diagram showing another embodiment of a scanning-beam generator.

FIG. 3b shows another embodiment of a scanning-beam generator 30b producing a scanning probe beam 4. The generator 30b includes an infrared-light source 32b, which produces an infrared-light beam 33b directed onto a disk 35b. The disk 35b holds a set of identical lenses 36b evenly distributed on a circle. A motor 34b rotates the disk 35b and the lenses 36b are scanned across the infrared-light beam 33b at a constant speed.

The infrared-light beam 38b transmitted through a lens 36b is focused onto a reference ring 20. As the lens 36b is scanned across the infrared-light beam 33b, the focused beam 38b is scanned across the reference ring 20. Thus, the focused infrared-light beam 38b may serve as the scanning probe beam 4 of FIG. 1.

Again, a beam splitter 39b directs a small portion of the beam 38b onto a reference photo-detector 40b. The output signal from the photo-detector 40b defines a reference point of the scanning and serves as the reference signal 31 of FIG. 1. In this embodiment, the infrared-fight source 32b is preferably either a pre-focused beam or a point source.

Figure 3C:
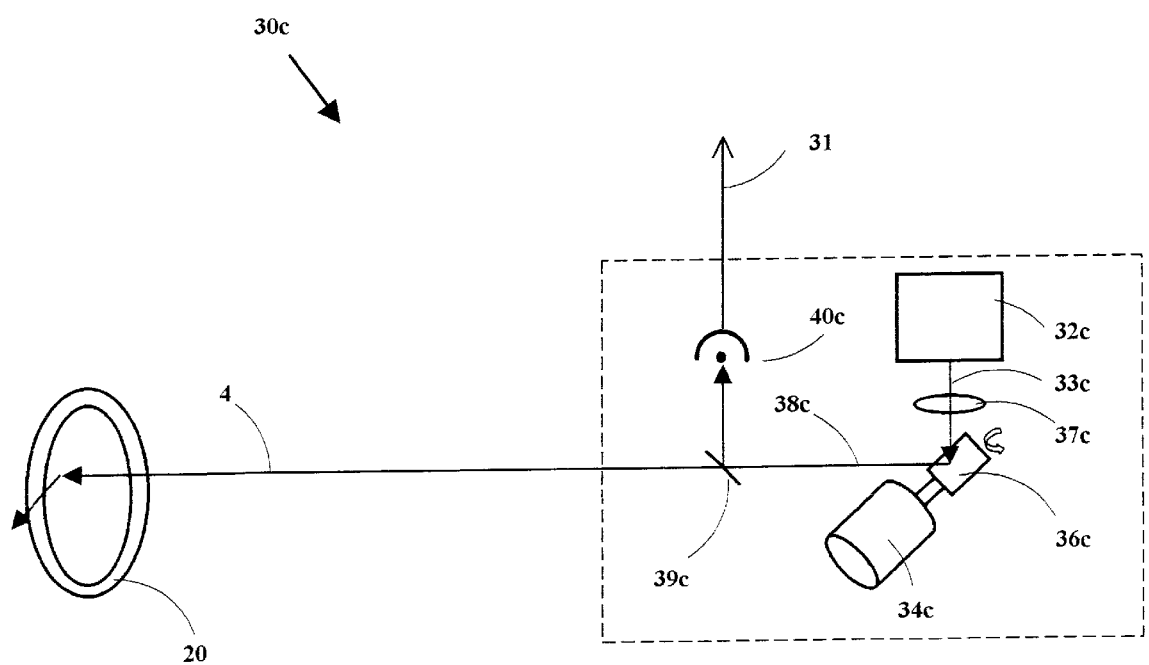
FIG. 3c is a schematic diagram showing a third embodiment of a scanning-beam generator.

FIG. 3c is a schematic diagram showing a third embodiment of a scanning-beam generator 30c producing a scanning probe beam 4. The generator 30c includes an infrared-light source 32c, which produces an infrared-light beam 33c directed into a lens 37c. The transmitted infrared beam 38c is reflected by a mirror 36c and focused onto a reference ring 20. The mirror 36c is driven by a scanner head 34c to scan the infrared beam 38c across the reference ring 20. Thus, the transmitted infrared beam 38a may serve as the scanning infrared beam 4 of FIG. 1. Similarly, a beam splitter 39c directs a small portion of the beam 38c onto a reference photo-detector 40c. The output signal from the photo-detector 40c defines the reference point of the scanning and serves as the reference signal 31 of FIG. 1. The scanner 34c scans the beam 38c back and forth. A synchronized signal from the scanner 34c can also be used as a reference point of the scanning. In this embodiment, the infrared-light source 32c can be either a collimated beam or a point source.

Figure 4:
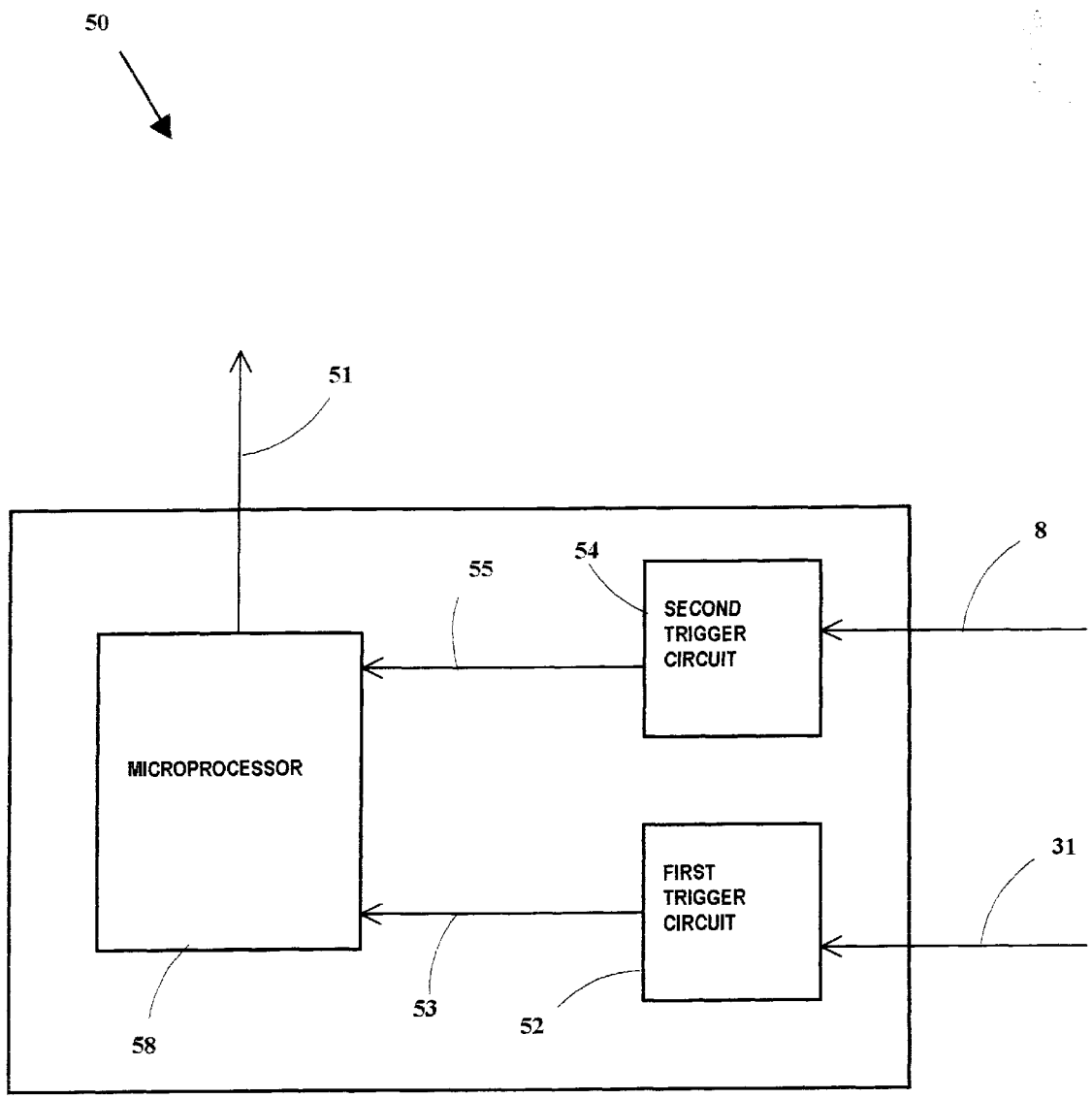
FIG. 4 is a block diagram showing a processing electronics for the optical monitoring and tracking systems of FIGS. 1 and 2.

FIG. 4 is a block diagram showing one embodiment of the processing electronics 50. This processing electronics 50 includes a first trigger circuit 52, a second trigger circuit 54, and a microprocessor 58. The reference signal 31 from the scanning beam generator 30 is fed into the first trigger circuit 52 to produce a TTL output signal 53 carrying the timing of the reference signal 31. The scattered-light signal 8 from the photo-detector 7 is fed into the second trigger circuit 54 to produce a TTL output signal 55 carrying the timing of the scattered-light signal 8.

The microprocessor 58 reads in the signal 53 and signal 55 to calculate a time delay Td between the two signals. This time delay Td indicates the relative position of the reference mark 20 to the scanning probe beam 4. This delay Td can be compared with an initial delay $Td_0$ registered and stored by the system computer 80 at the very beginning of the tracking.

For an open loop device 100, any change of the delay Td from its initial value Tdo can be used to determine a displacement of the eye 10 from its initial position. The determined displacement can then be converted into an offset signal combined in the control signal 81 to deflect the surgical laser beam 62 to follow the movement of the eye 10.

For a close loop device 200, any deviation of the delay Td from its initial value $Td_0$ is used as an error signal to drive the beam steering module 60 such that to bring the error signal toward zero. The beam steering module 60 thus deflects both of the scanning probe beam 4 and the surgical laser beam 62 to follow the movement of the eye 10.

The above-described operation of the processing electronics 50 is repetitively for every scan of the probe beam 4. The first trigger circuit 52 and the second trigger circuit 54 should be reset automatically after the signal 53 and signal 55 are read by the microprocessor 58.

The processing electronics 50 shown in FIG. 4 is for one axis tracking. To track the two-dimensional movement of the eye 10, another pair of the trigger circuit should be used.

Figure 5A:
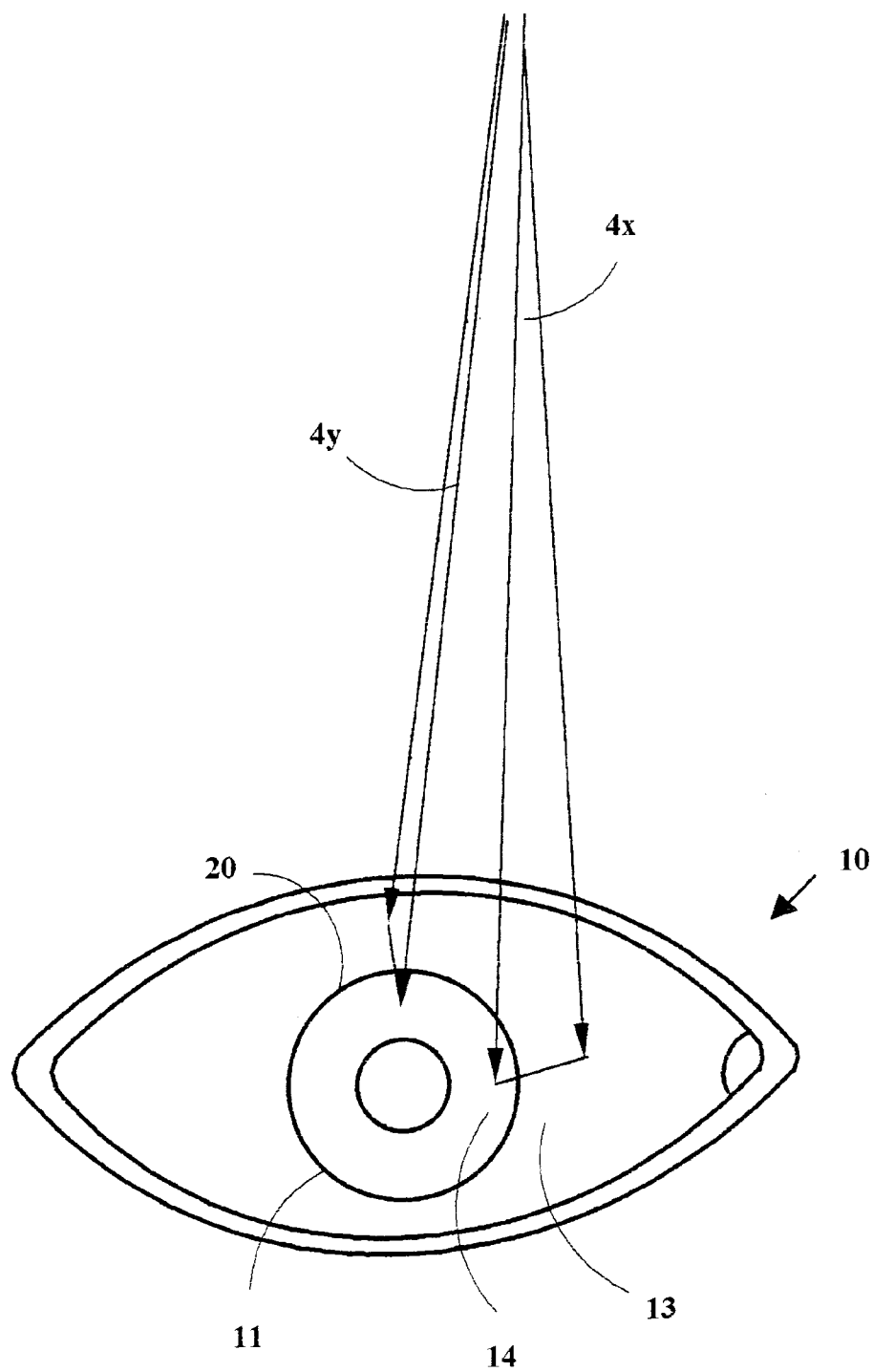
FIG. 5a is a schematic diagram illustrating simultaneous tracking of an eye in two different directions by two scanning probe beams projected on the limbus.

FIG. 5a shows schematically two scanning probe beams 4x and 4y projected on a reference ring 20 (the limbus 11) for two-dimension positioning detection. The two scanning probe beams 4x and 4y are set along two approximately perpendicular directions and occupy about one quart of the limbus 11.

Figure 5B:
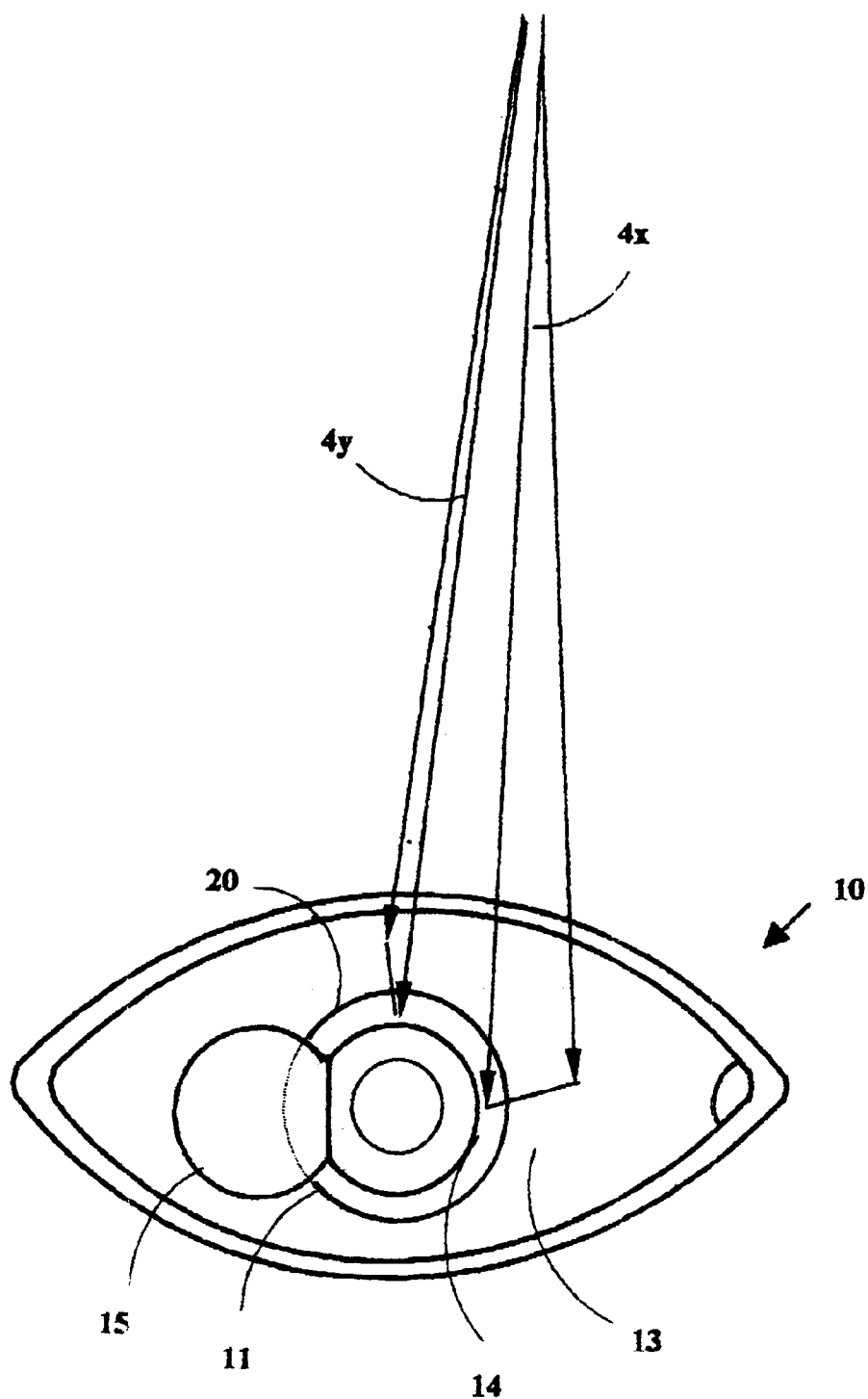
FIG. 5b shows two scanning probe beams projected on a partially obscured limbus to track the eye movement in two different directions in a LASIK surgery.

FIG. 5b shows how the tracking device remains full performance for LASIK. In a LASIK surgery, a disk shape flap is laminated from the cornea and about one quart of the perimeter is uncut to maintain the flap attached to the cornea. The flap is folded over during the surgery to allow laser ablation on the corneal bed. The folded flap 15 covers about one third of the limbus 11 and may disable those eye tracking devices which rely on the whole limbus as the reference. The corneal bed after the flap is folded becomes less smooth and the scattered light from the corneal bed may disturb those tracking devices that use the pupil as a reference.

As illustrated in FIG. 5b, the two scanning beams 4x and 4y use only the limbus section that is not covered by the cornea flap 15. Therefore, the limbus 11 remains as a good reference for the tracking device of the present invention.

In all the above description, the tracking device is to steer a surgical laser beam 62 to follow the eye movement. Obviously, the same tracking mechanism can guide any other light beam or simply an optical path to follow the eye movement. Therefore, the above techinque an be used to other surgical or diagnosis application in which compensating the eye movement is desirable.

Although the above embodiments are described with a specific reference to eye tracking, the techniques can be generally used to track lateral movement of other object with an optical reference mark. Various modifications can be made without departing from the scopes of the appended claims.

What is claimed is:

1. An optical device adopted to track lateral movement of an object, comprising:
   a scanning beam generator to generate and to scan a probe beam in a predetermined spatial pattern across a portion of the object that includes a reference mark, wherein the scattered light from said object has a sharp change when said probe beam scans across the boundary of said reference mark;
   an optical assembly collecting said scattered light from said object;
   a photo-detector receiving said scattered light to produce a scattered-light signal indicating the change caused by said reference mark; and
   a processing electronics, coupled to said scanning beam generator and said photo-detector, to process the scattered-light signal and to determine a position change of said reference mark with respect to a reference position so as to track movement of said object.

2. A device as in claim 1, wherein said scanning beam generator comprising:
   a light source producing a light beam;
   a wheel having a plurality of pinholes evenly arranged in a circle and positioned relative to said light beam in a way that each pinhole intercepts said light beam as said wheel rotates around a rotation axis; and
   a lens positioned relative to said wheel to project an scanning image of each pinhole onto said object when said pinhole is rotated into the path of said light beam.

3. A device as in claim 1, wherein the scanning beam generator comprising;
   a light source producing a probe beam;
   a wheel having a plurality of apertures evenly arranged in a circle and positioned relative to said probe beam in a way that each aperture intercepts said probe beam as said wheel rotates around a rotation axis, each aperture including a lens to project said probe beam to said object wherein said probe beam scans repetitively across said object as said lenses rotate with said wheel.

4. A device as in claim 1, wherein the scanning beam generator comprising:
   a light source to produce a probe beam;
   a mirror which moves to scan repetitively said probe beam across said object.

5. A device as in claim 1, wherein said object is an eye and said reference mark is a portion of the limbus.

6. A device as in claim 1, further comprising:
   a beam steering module to direct a laser beam onto said object; and
   a control unit coupled to said processing electronics and generating a control signal to drive said beam steering module, said control unit may include a computer and said control signal consists of an offset signal to compensate for position change of said object;
   wherein said beam steering module directs said laser beam to a desired position on said object regardless of the movement of said object.

7. A device as in claim 1, further comprising:
   a beam steering module disposed in the path of said probe beam to direct said probe beam onto said object; and
   a control unit coupled to said processing electronics and generating a control signal to drive said beam steering module, said control unit may include a computer and said control signal is to minimize any position change of said reference mark with respect to said reference position;
   wherein a close-loop control can substantially maintain stationary the trace of said probe beam with respect to said reference mark on said object.

8. A method for optically tracking lateral movement of an object, comprising the steps of:
   selecting a reference mark on said object;
   scanning a probe beam in a predetermined spatial pattern across said reference mark;
   producing a reference signal from said probe beam to represent a reference position in the predetermined spatial pattern;
   detecting scattered light of said probe beam from said object to produce a scattered-light signal, said scattered-light signal has a sequence of sharp steps of which the timing depends on the position of said reference mark; and
   comparing said scattered-light signal and said reference signal to determine the relative position of said reference mark with respect to said reference position so as to track said object.

9. A method as in claim 8, further comprising the steps of:
   using a beam steering module to direct a laser beam to said object; and
   controlling said beam steering module according to said relative position of said reference mark with respect to said reference position so that the direction of said laser beam is compensated for the movement of said object.

10. A method as in claim 8, further comprising the steps of:
    using a beam steering module to direct said probe beam onto said object; and
    controlling in a close-loop manner said beam steering module to substantially maintain stationary said relative position of said reference mark with respect to said reference position.

11. An apparatus for tracking eye movement comprising:
    a scanning beam generator projecting a scanning probe beam repeatedly across a reference mark on a subject eye, said scanning beam generator also producing a reference signal synchronized with said scanning probe beam;
    an optical assembly collecting the scattered light of said scanning probe beam from said subject eye;
    a photo-detector receiving said scattered light to produce a scattered-light signal, said scattered-light signal has a sequence of sharp steps of which the timing depends on the position of said reference mark; and
    a processing electronics read in said reference signal and said scattered-light signal to determine any position change of said reference mark;
    whereby a control unit coupled to said processing electronics can generate a control signal to steer an optical path to follow the movement of said subject eye.

12. An apparatus as defined in claim 11 wherein said reference object is the limbus of the eye.

13. An apparatus as defined in claim 11 wherein said scanning beam generator consists of a set of rotating pinholes.

14. An apparatus as defined in claim 11 wherein said scanning beam generator consists of a set of rotating lenses.

15. An apparatus as defined in claim 11 wherein said scanning beam generator consists of a scanner.

16. An apparatus as defined in claim 11 wherein said optical assembly consists of a lens or a set of lenses.

17. An apparatus as defined in claim 11 wherein said processing electronics consists of a set of trigger circuits.

18. An apparatus as defined in claim 11 wherein said optical path represents a surgical laser beam.

19. An apparatus as defined in claim 11 wherein said optical path represents a diagnosis light beam or an observation path.

20. An apparatus as defined in claim 11 wherein a second set of said scanning beam generator and said photo-detector are used to determine the eye's movement at a second axis orthogonal to the first axis, so as to track the eye's movement in two dimensions.

* * * * *